(12) United States Patent
Zhao et al.

(10) Patent No.: US 10,036,707 B2
(45) Date of Patent: Jul. 31, 2018

(54) GEM IDENTIFICATION METHOD AND APPARATUS

(71) Applicants: Nuctech Company Limited, Haidian District, Beijing (CN); Tsinghua University, Haidian District, Beijing (CN)

(72) Inventors: Ziran Zhao, Beijing (CN); Li Zhang, Beijing (CN); Yingying Geng, Beijing (CN); Hongqiu Wang, Beijing (CN); Yumin Yi, Beijing (CN)

(73) Assignees: Nuctech Company Limited, Haidian District, Beijing (CN); Tsinghua University, Haidian District, Beijing (CN)

( * ) Notice: Subject to any disclaimer, the term of this patent is extended or adjusted under 35 U.S.C. 154(b) by 772 days.

(21) Appl. No.: 14/576,752

(22) Filed: Dec. 19, 2014

(65) Prior Publication Data
US 2015/0185155 A1    Jul. 2, 2015

(30) Foreign Application Priority Data

Dec. 27, 2013    (CN) .......................... 2013 1 0741368

(51) Int. Cl.
*G01N 21/65*    (2006.01)
*G01J 3/28*    (2006.01)
(Continued)

(52) U.S. Cl.
CPC ................ *G01N 21/65* (2013.01); *G01J 3/28* (2013.01); *G01J 3/44* (2013.01); *G01N 21/87* (2013.01);
(Continued)

(58) Field of Classification Search
CPC .... G01N 21/65; G01N 21/87; G01N 2201/12; G01N 2201/06113; G01J 3/44; G01J 3/28; G01J 3/4412
See application file for complete search history.

(56) References Cited

U.S. PATENT DOCUMENTS

| | | |
|---|---|---|
| 4,012,141 A | 3/1977 | Hanneman |
| 4,799,786 A | 1/1989 | Gerrard |
| | (Continued) | |

FOREIGN PATENT DOCUMENTS

| | | |
|---|---|---|
| CH | 700 695 A2 | 9/2010 |
| CN | 1385691 A | 12/2002 |
| | (Continued) | |

OTHER PUBLICATIONS

International Search Report for corresponding International Patent Application No. PCT/CN2014/094982 dated Mar. 30, 2015.
(Continued)

*Primary Examiner* — John Breene
*Assistant Examiner* — Mohammad Islam
(74) *Attorney, Agent, or Firm* — Merchant & Gould P.C.

(57) ABSTRACT

Embodiments of the present invention provide jewel and jade identification method and apparatus. The method comprises the steps: (a) placing a sample to be detected over a light transmission hole formed on a carrying surface of an object table and emitting, by an optical probe disposed below the carrying surface, an exciting light onto the sample through the light transmission hole and then collecting a Raman scattered light from the sample by the optical probe. (b) acquiring a Raman spectrum curve of the sample from the collected Raman scattered light from the sample; and (c) comparing the Raman spectrum curve with a reference Raman spectrum library for jewels and jades to identify the
(Continued)

sample. The method and apparatus may achieve effective, convenient and accurate inspections of the jewels and jades.

11 Claims, 6 Drawing Sheets

(51) Int. Cl.
    *G01N 21/87*     (2006.01)
    *G01J 3/44*     (2006.01)
(52) U.S. Cl.
    CPC ... *G01J 3/4412* (2013.01); *G01N 2201/06113* (2013.01); *G01N 2201/12* (2013.01)

(56) References Cited

U.S. PATENT DOCUMENTS

| | | | | |
|---|---|---|---|---|
| 5,811,817 | A * | 9/1998 | Ravich | G01N 21/87 |
| | | | | 250/372 |
| 6,278,518 | B1 * | 8/2001 | Schrof | G01N 15/04 |
| | | | | 356/318 |
| 6,583,879 | B1 | 6/2003 | Berg et al. | |
| 2004/0064259 | A1 | 4/2004 | Haaland et al. | |
| 2007/0104061 | A1 | 5/2007 | Aufderheide et al. | |
| 2008/0221457 | A1 * | 9/2008 | Zeng | A61B 5/0071 |
| | | | | 600/477 |
| 2011/0261354 | A1 * | 10/2011 | Sinfield | G01J 3/02 |
| | | | | 356/301 |
| 2011/0292376 | A1 | 12/2011 | Kukushkin et al. | |
| 2012/0125998 | A1 | 5/2012 | Magill | |
| 2012/0126142 | A1 * | 5/2012 | Matsui | G01N 21/6452 |
| | | | | 250/459.1 |
| 2012/0320375 | A1 * | 12/2012 | Lipson | G01N 21/01 |
| | | | | 356/246 |
| 2013/0271750 | A1 | 10/2013 | Xu et al. | |
| 2013/0297254 | A1 | 11/2013 | Vignesh et al. | |
| 2013/0321792 | A1 * | 12/2013 | Shapiro | G01N 21/65 |
| | | | | 356/30 |
| 2014/0118733 | A1 * | 5/2014 | Harward | G01N 21/65 |
| | | | | 356/301 |

FOREIGN PATENT DOCUMENTS

| | | |
|---|---|---|
| CN | 103293140 A | 9/2013 |
| EP | 1 305 608 A1 | 5/2003 |
| JP | 52-166583 U | 12/1977 |
| JP | H01-161123 A | 6/1989 |
| JP | H10-501333 A | 2/1998 |
| JP | 2008-129017 A | 6/2008 |
| JP | 2008-268059 A | 11/2008 |
| JP | 2010-527017 A | 8/2010 |
| JP | 2011-043472 A | 3/2011 |
| JP | 2013-522648 A | 6/2013 |

OTHER PUBLICATIONS

Written Opinion of the International Searching Authority for corresponding International Patent Application No. PCT/CN2014/094982 dated Mar. 30, 2015, with English translation.

Chinese Office Action for corresponding Chinese Patent Application No. 201310741368.9 dated Jul. 28, 2017, 7 pages. (Rejecting all claims over CN103293140A and listing US2013/0321792A1 as a relevant reference.)

Extended European Search Report for corresponding European Patent Application No. 14873997.2 dated Jun. 30, 2017, 10 pages.

Bersani, D. et al., "Applications of Raman Spectroscopy to Gemology", Analytical and Bioanalytical Chemistry, 397(7): 2631-2646 (2010).

* cited by examiner

GEM IDENTIFICATION METHOD AND APPARATUS

CROSS-REFERENCE TO RELATED APPLICATION

This application claims the benefit of Chinese Patent Application No. 201310741368.9 filed on Dec. 27, 2013 in the State Intellectual Property Office of China, the whole disclosure of which is incorporated herein by reference.

BACKGROUND OF THE INVENTION

Field of the Invention

The present disclosure relates to the technical field of gem detection, and in particular, to a gem identification method using Raman spectroscopy and a gem identification apparatus.

Description of the Related Art

As corporeal culture standard of living rises, requirements to gems, for example jewels or jades, are increasing. It facilitates the development of market of gems. However, as the market of gems is growing, emergence of various artificial gems and fakes disturbs the normal development of the market. Thus identification of gems becomes more and more important. Conventional identification methods of gems include such as observation by a magnifier, hardness inspection, refractivity inspection and observation by a microscope. These methods have single parameter and low precision and cannot identify the matter uniquely. Meanwhile, these technologies depend on the knowledge accumulation and experiences of the identifiers to a great extent. Some novel gem identification methods for example include thermal reaction, chemical reaction, Mohs hardness, thermal conductivity, infrared light, ultraviolet light, visible light, X ray diffraction analysis.

SUMMARY OF THE INVENTION

An embodiment of the present invention provides a gem identification method, comprising the steps of:

(a) placing a sample to be detected over a light transmission hole on a carrying surface of an object table and emitting, by an optical probe disposed below the carrying surface, an exciting light onto the sample through the light transmission hole and then collecting a Raman scattered light from the sample by the optical probe;

(b) acquiring a Raman spectrogram of the sample from the collected Raman scattered light from the sample; and (c) comparing the Raman spectrogram with a reference Raman spectrogram library for gems to identify the sample.

An embodiment of the present invention provides a gem identification apparatus comprising:

an object table having a carrying surface configured to carry a sample to be detected thereon, the carrying surface being formed with one or more light transmission holes corresponding to one or more measure positions respectively;

an optical probe disposed below the carrying surface and configured to emit an exciting light onto the corresponding measure position through one of the light transmission holes from the underside of the carrying surface and then collect a Raman scattered light from the sample from the corresponding measure position; and a data process device configured to generate a Raman spectrogram from the Raman scattered light collected from the sample and then compare the Raman spectrogram with a reference Raman spectrogram library for gems to identify the sample.

DETAILED DESCRIPTION OF PREFERRED EMBODIMENTS OF THE INVENTION

Figure 1:
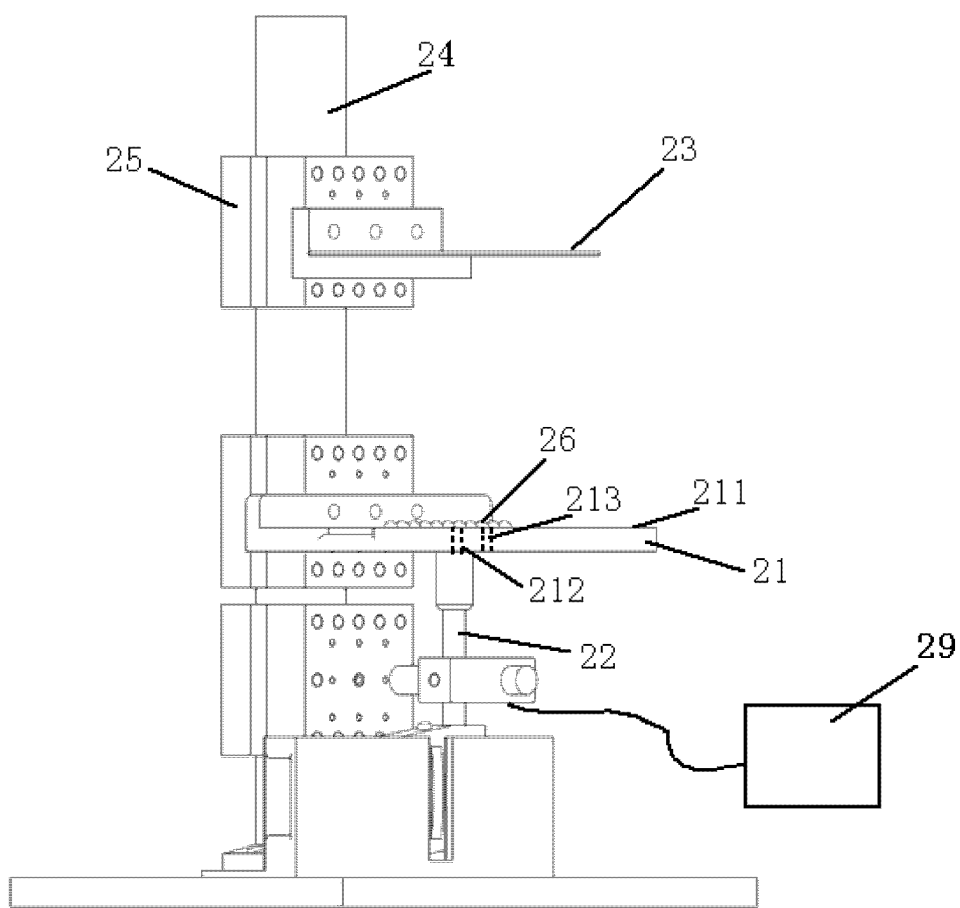
FIG. 1 shows schematically a perspective view of a gem identification apparatus according to an embodiment of the present invention.

Exemplary embodiments of the present invention will be described hereinafter in detail with reference to the attached drawings, wherein the like reference numerals refer to the like elements. The present invention may, however, be embodied in many different forms and should not be construed as being limited to the embodiment set forth herein; rather, these embodiments are provided so that the present invention will be thorough and complete, and will fully convey the concept of the disclosure to those skilled in the art.

Figure 2:
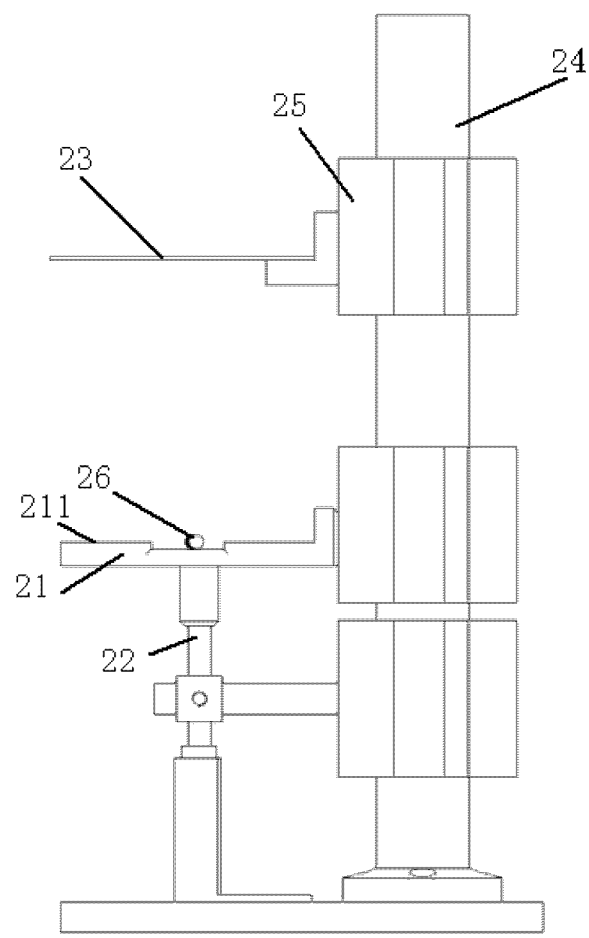
FIG. 2 shows schematically a side view of a gem identification apparatus according to an embodiment of the present invention.

FIGS. 1-2 show schematically a perspective view and a side view of a gem identification apparatus according to an embodiment of the present invention, respectively. The gem identification apparatus 20 may include an object table 21, an optical probe 22 and a data process device 29. The object table 21, for example in form of a bracket, a tray or a support plate, may have a carrying surface 211 configured to carry a sample 26 to be detected thereon, and the carrying surface 211 is formed with light transmission holes 212, 213 corresponding to measure positions respectively. One or more light transmission holes may be formed, thus, one or more corresponding measure positions may also be provided. The optical probe 22 is located below the carrying surface 211 and is configured to emit an exciting light onto the corresponding measure position through the light transmission holes 212, 213 from the underside of the carrying surface 111 and then collect a Raman scattered light from the sample 26 from the corresponding measure position. The data process device 29 may be configured to generate a Raman spectrogram from the collected Raman scattered light and then compare the Raman spectrogram with a reference Raman spectrogram library for gems, so as to identify the sample 26 to be detected.

In an embodiment of the present invention, the sample 26 to be detected, for example a string of gems, is placed on the carrying surface 211 and the optical probe 22 emits the exciting light onto the sample 26 to be detected through the light transmission hole 212, 213 on the carrying surface 211 from the underside of the carrying surface 111. In comparison with the conventional case that the optical device is arranged above the sample to be detected, on one hand, it may prevent the optical device from interfering with the retrieval of the sample 26 to be detected; on the other hand, it may keep a stable distance between the sample 26 to be detected and the light emitting opening of the optical probe 22, for example, it may make the focal position of the exciting light to be located adjacent to the light transmission hole 212, 213, which accurately ensures multiple measurements of the sample 26 or measurements of a plurality of samples 26 to be performed by the same illumination intensity without adjusting the relative position between the optical probe 22 and the sample 26 every time, so as to suppress errors caused by inconsistency of measurements. Further, since the relative position between the optical probe 22 and the sample 26 does not need to be adjusted every time, the gem identification apparatus 20 may be easily applied in fast inspection of strings of samples 26. For example, for a string of gems, as long as the string of gems are moved on the carrying surface 211 such that the gems in the string are arranged in sequence at the light transmission holes 212, 213, the fast inspection for each of the gems in the string may be done.

As an example, the optical system of the optical probe 22 may be composed of separate optical elements, or the optical probe 22 may be a fiber probe. As an example, the optical probe 22 may include a laser source, or the laser source may be separate to the optical probe 22. In an example, the laser may have a wavelength of 785 nm. Alternatively, other wavelengths may also be used. As an example, the optical probe 22 may also include a necessary control unit, for example, a laser drive and control unit, or the control unit may alternatively be arranged outside the optical probe 22, for example, arranged in the data process device.

As an example, the data process device may have a reference Raman spectrogram library including reference Raman spectrograms of the gem samples having known compositions and reference Raman spectrograms of fakes, such as plastics, glass, for comparison. The data process device may also have a specialized tool, to help the user to collect and establish or replenish the reference Raman spectrogram library.

As an example, as illustrated in FIGS. 1-2, the gem identification apparatus 1 may further include a shielding baffle 23 and a sliding track 24 carrying the shielding baffle 23. The shielding baffle 23 is located above the carrying surface 26 and is slidable in a vertical direction along the sliding track 24. In an example, the shielding baffle 23 may be mounted on a movable slide block 25 and be slidably connected to the sliding track 24 by the movable slide block 25. The shielding baffle 23 is configured to shield the light transmission hole from the upside of the carrying surface 211 in detection to prevent the user's eyes from being injured by the exciting light.

In an example, the diameters of the light transmission holes 212, 213 are variable. In terms of gems, their different parts may be made of different compositions. Thus, sometimes, it needs to specifically detect a certain small local part of the sample 26 to be detected. In order to accurately direct the exciting light onto the desired local part of the sample 26 to prevent the other parts of the sample 26 from disturbing the detection results, the diameters of the light transmission holes 212, 213 may be reduced. In contrast, when it needs to detect a more large local part of the sample 26, the diameters of the light transmission holes 212, 213 may be enlarged to allow larger amount of the exciting light to reach the sample 26 so as to avoid the intensity loss and to improve the signal-to-noise ratio.

As discussed above, there may be one or more light transmission holes 212, 213. For example, the carrying surface 26 may have a first light transmission hole 212 corresponding to a first measure position and a second light transmission hole 213 corresponding to a second measure position. The object table 21 is movable with respect to the optical probe 22 in a horizontal direction such that the measure position corresponding to the optical probe 22 is switchable between the first measure position and the second measure position. It means that when different samples 26 are arranged at different light transmission holes, for example, the first light transmission hole 212 and the second light transmission hole 213, different samples 26 may be switched for detection by shifting the object table 21 instead of moving the samples one by one. It will be helpful to improve efficiency of fast inspection, in particular if many light transmission holes are provided. For example, the samples 26 to be detected may be loaded/unloaded on both sides of the object table 21 along the direction in which it shifts, and the samples 26 may be switched one by one by shifting the object table 21 back and forth to improve efficiency.

Figure 3:
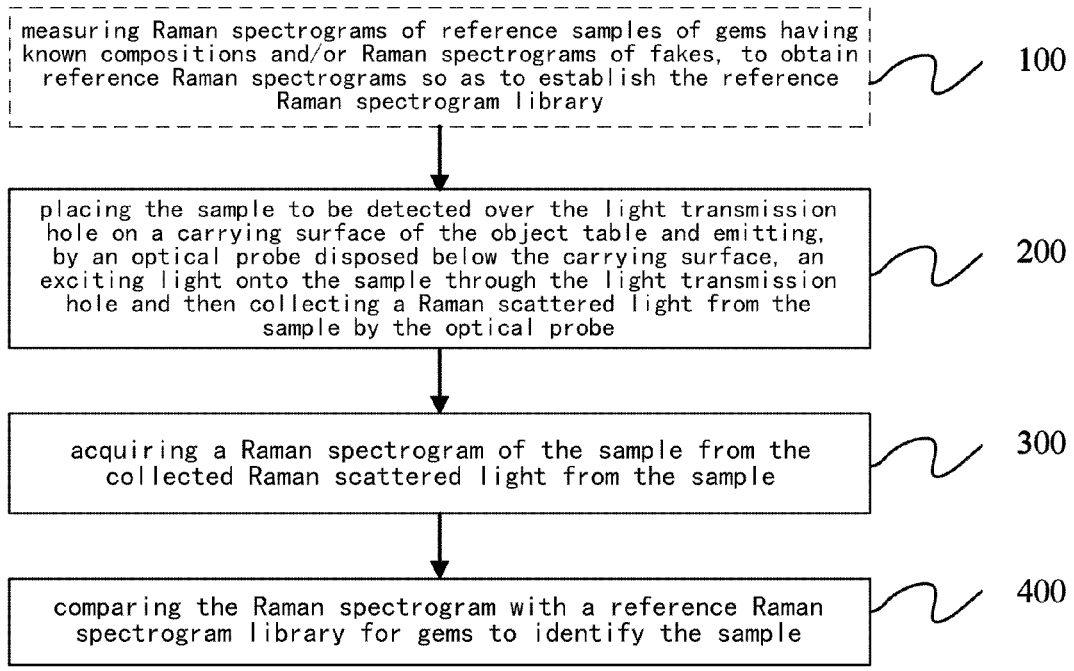
FIG. 3 shows a schematic flow chart of a gem identification method according to an embodiment of the present invention.

FIG. 3 shows a schematic flow chart of a gem identification method 10 according to an embodiment of the present invention. As illustrated in the solid block in FIG. 3, the gem identification method 10 may include the steps of:

Step 200: placing the sample 26 to be detected over the light transmission hole 212 on a carrying surface 211 of the object table 21 and emitting, by an optical probe disposed below the carrying surface, an exciting light onto the sample 26 through the light transmission hole 212 and then collecting a Raman scattered light from the sample 26 by the optical probe;

Step 300: acquiring a Raman spectrogram of the sample 26 from the collected Raman scattered light from the sample 26; and Step 400: comparing the Raman spectrogram with a reference Raman spectrogram library for gems to identify the sample 26.

As an example, as indicated by the dashed block in FIG. 3, the gem identification method 10 may further include, before the above Step 200, the following optional step of:

Step 100: measuring Raman spectrograms of reference samples of gems having known compositions and/or Raman spectrograms of fakes, to obtain reference Raman spectrograms so as to establish the reference Raman spectrogram library.

In the above embodiments of the present invention, the reference Raman spectrogram library may be collected in field, or may have been collected in advance, even may be a commercially available module of reference Raman spectrogram library.

Figure 4:
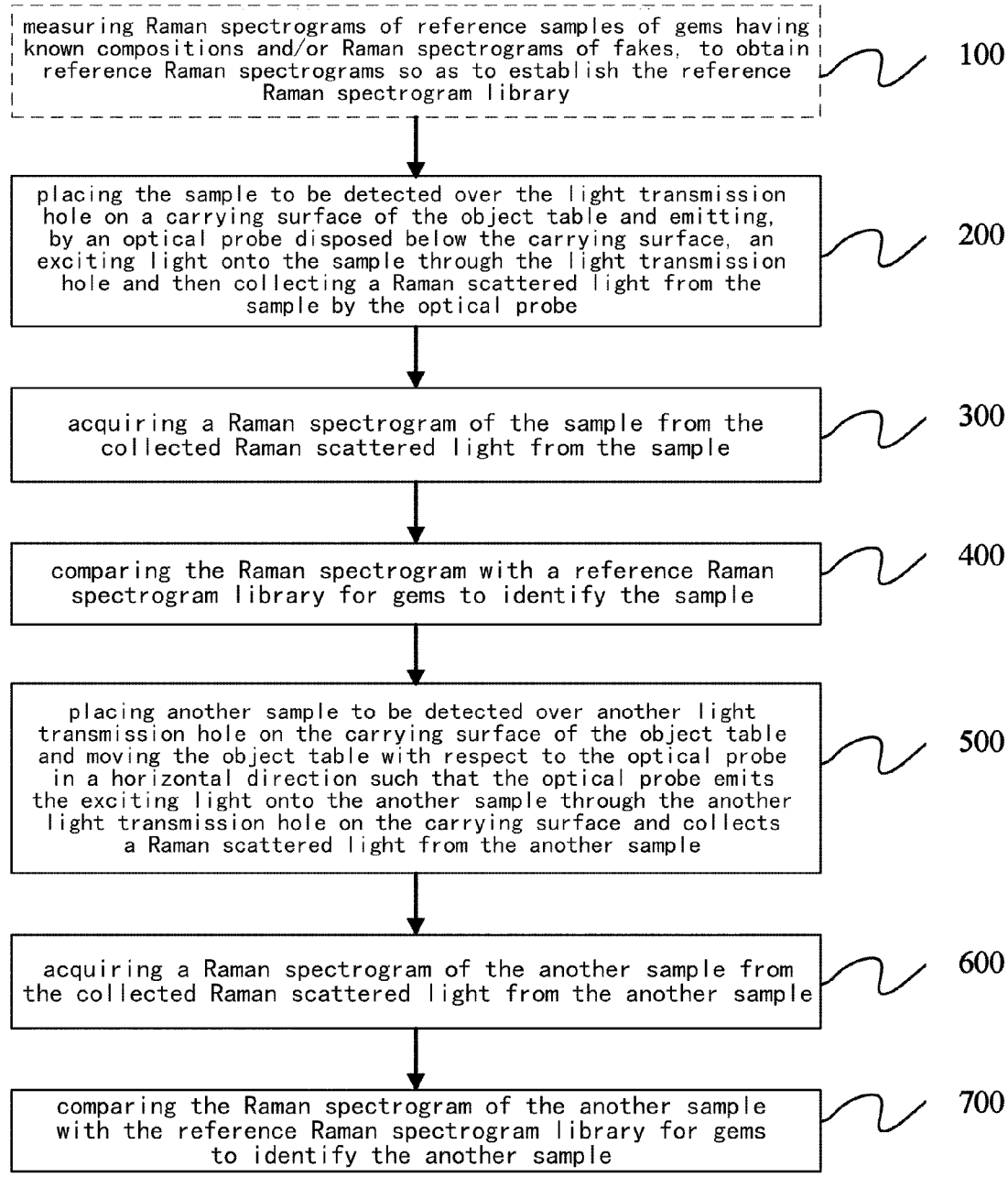
FIG. 4 shows a schematic flow chart of a gem identification method according to another embodiment of the present invention.

FIG. 4 shows a schematic flow chart of a gem identification method 10' according to an embodiment of the present invention. In the gem identification method 10', more than one light transmission holes are used. It is distinguished from the gem identification method 10 shown in FIG. 3 in that it further includes the steps of:

Step 500: placing another sample 26 to be detected over another light transmission hole 213 on the carrying surface 211 of the object table 21 and moving the object table 21 with respect to the optical probe 22 in a horizontal direction such that the optical probe 22 emits the exciting light onto the another sample 26 through the another light transmission hole 213 on the carrying surface 211 and collects a Raman scattered light from the another sample 26;

Step 600: acquiring a Raman spectrogram of the another sample 26 from the collected Raman scattered light from the another sample 26; and Step 700: comparing the Raman spectrogram of the another sample 26 with the reference Raman spectrogram library for gems to identify the another sample 26.

The skilled person in the art would appreciate that, although the above example is explained only with reference to two light transmission holes, more light transmission holes may alternatively be used and these light transmission holes may be switched by shifting the object table 21 in order to replace different samples 26 to be detected. As discussed above, by means of the structures with more than one light transmission holes, the detection efficiency may be further improved. It is in particular advantageous in the fast inspection.

Figure 5:
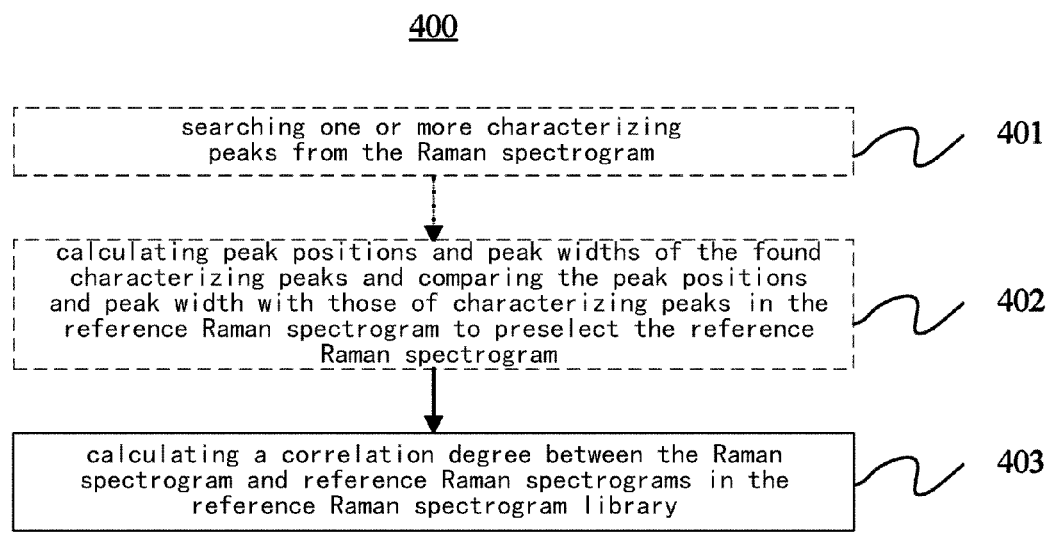
FIG. 5 is a schematic flow chart showing steps of comparing a Raman spectrogram of the sample to be detected with a reference Raman spectrogram library for gems according to an embodiment of the present invention.

FIG. 5 schematically shows an example of the Step 400 in the gem identification method 10, 10'. In this example, the Step 400 may include:

Step 403: calculating a correlation degree between the Raman spectrogram and reference Raman spectrograms in the reference Raman spectrogram library.

The above correlation degree may be calculated by various methods. For example, if A(x) is a Raman spectrogram function of the sample to be detected and B(x) is a reference Raman spectrogram function, in an example, the above correlation degree may be calculated on basis of the following equation (1):

$$\text{Corr} = \left(1 - \sqrt{1 - \frac{A(x) \cdot B(x)}{\sqrt{A(x) \cdot A(x)} \sqrt{B(x) \cdot B(x)}}}\right) \times 100 \quad (1)$$

where Corr is the correlation degree between the Raman spectrogram and the reference Raman spectrogram, the operator of "●" represents dot product operation.

In another example, A(x) and B(x) may be sampled respectively to obtain their respective n sample points. These sample points are defined as $A_1, A_2, \ldots, A_n$ and $B_1, B_2, \ldots, B_n$, respectively. The correlation degree Corr between the Raman spectrogram and the reference Raman spectrogram may be calculated on basis of the following equation (2):

$$\text{Corr} = \frac{\left(\left(A(x) - \frac{\sum_{i=1}^{n} A_i}{n}\right) \cdot \left(B(x) - \frac{\sum_{i=1}^{n} B_i}{n}\right)\right)^2}{\left(\left(A(x) - \frac{\sum_{i=1}^{n} A_i}{n}\right) \cdot \left(A(x) - \frac{\sum_{i=1}^{n} A_i}{n}\right)\right)} \times 100\% \quad (2)$$

$$\left(\left(B(x) - \frac{\sum_{i=1}^{n} B_i}{n}\right) \cdot \left(B(x) - \frac{\sum_{i=1}^{n} B_i}{n}\right)\right)$$

where the operator of "●" also represents dot product operation.

In another example, A(x) and B(x) may be sampled respectively to obtain their respective n sample points. These sample points are defined as $A_1, A_2, \ldots, A_n$ and $B_1, B_2, \ldots, B_n$, respectively. The correlation degree Corr between the Raman spectrogram and the reference Raman spectrogram may be calculated on basis of the following equation (3):

$$\text{Corr} = \left(1 - \frac{\sum_{i=1}^{n} |A_i - B_i|}{n}\right) \times 100\%. \quad (3)$$

The above calculations of the correlation degree may be performed for whole Raman spectrogram, or may be performed for local part with the characterizing portion in the Raman spectrogram. Regarding the calculation method of the correlation degree between the Raman spectrogram and the reference Raman spectrogram of the another sample to be detected, it is substantially same to the above calculation method of the correlation degree between the Raman spectrogram and the reference Raman spectrogram. Thus, its detailed description will be omitted below. The above paragraphs only give some examples of calculation of the correlation degree. Alternatively, other calculation methods of the correlation degree in the art are also applicable.

If the correlation degree between the Raman spectrogram and the reference Raman spectrogram exceeds a predetermined threshold, it can be determined that the compositions of the sample to be detected are identical to the compositions of the sample corresponding to the reference Raman spectrogram, to achieve the identification of the sample to be detected. In contrast, if it is less than the predetermined threshold, it can be determined that the compositions of the sample to be detected are not identical to the compositions of the sample corresponding to the reference Raman spectrogram. The predetermined threshold may be given depending on factors such as practical requirements for detection, precision of the detection instrument.

As shown, the Step 400 may further include, before the Step 403, the following two optional steps of:

Step 401: searching one or more characterizing peaks from the Raman spectrogram; and Step 402: calculating peak positions and peak widths of the found characterizing peaks and comparing the peak positions and peak width with those of characterizing peaks in the reference Raman spectrogram to preselect the reference Raman spectrogram to be used in the calculation of the Step 403.

As many kinds of gems may be used, in identification of gems, it may need to compare the Raman spectrogram of the sample 26 to be detected with a plurality of reference Raman spectrograms respectively. If the correlation degree is calculated on basis of each of the reference Raman spectrograms, the computation complexity would become large. By means of the above Steps 401, 402, the reference Raman spectrograms that are distinguished significantly from the Raman spectrogram of the sample 26 to be detected may be removed by performing peak seeking and selecting processes, so as to reduce the computation complexity in the Step 403. Upon seeking of the characterizing peaks and calculating of the peak widths and peak positions, for example, two upper and lower thresholds may be estimated using the statistical distribution of peak signal in the Raman spectrograms. In the seeking process, when the signal amplitude is above the upper threshold, it can be determined that a peak is found. Further, forward and backward seeking will be performed continuously until the points below the lower threshold are found. The points below the lower threshold may be considered as the starting point and the terminal point of the peak. The parameters such as peak heights and peak widths may be further calculated. However, the present invention is not limited to this, other methods for seeking the characterizing peaks and calculating peak widths and peak positions are also applicable.

In addition, as an example, if characterizing peaks of the Raman spectrogram of the sample 26 to be detected is significant, in practice, calculation of the correlation degree may even be simplified to seek whether or not there are characterizing peaks corresponding to the characterizing peaks of the reference Raman spectrograms at one or more positions in the Raman spectrogram of the sample to be detected, so as to directly determine the correlation degree.

Figure 6:
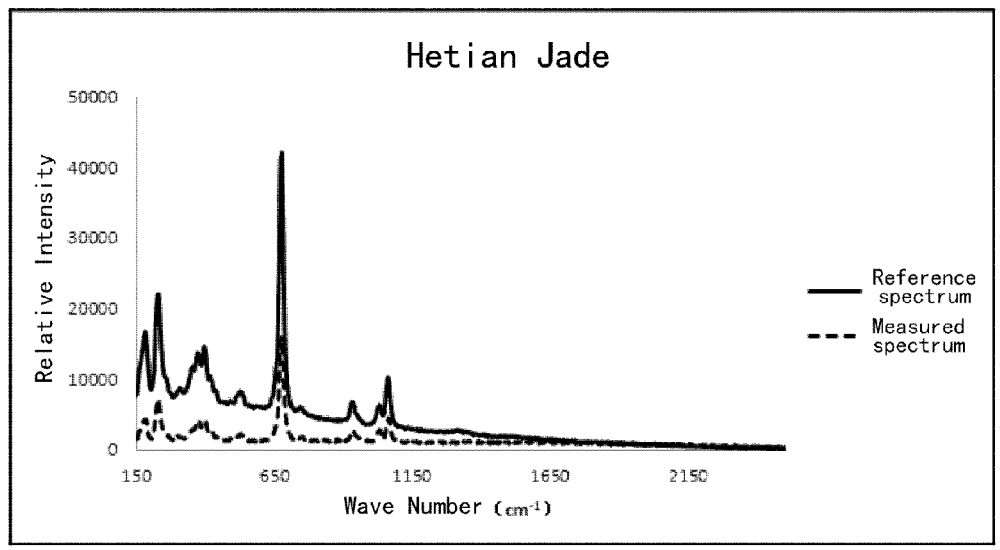
FIGS. 6-7 show identification examples of the gem identification method according to an embodiment of the present invention.
Figure 7:
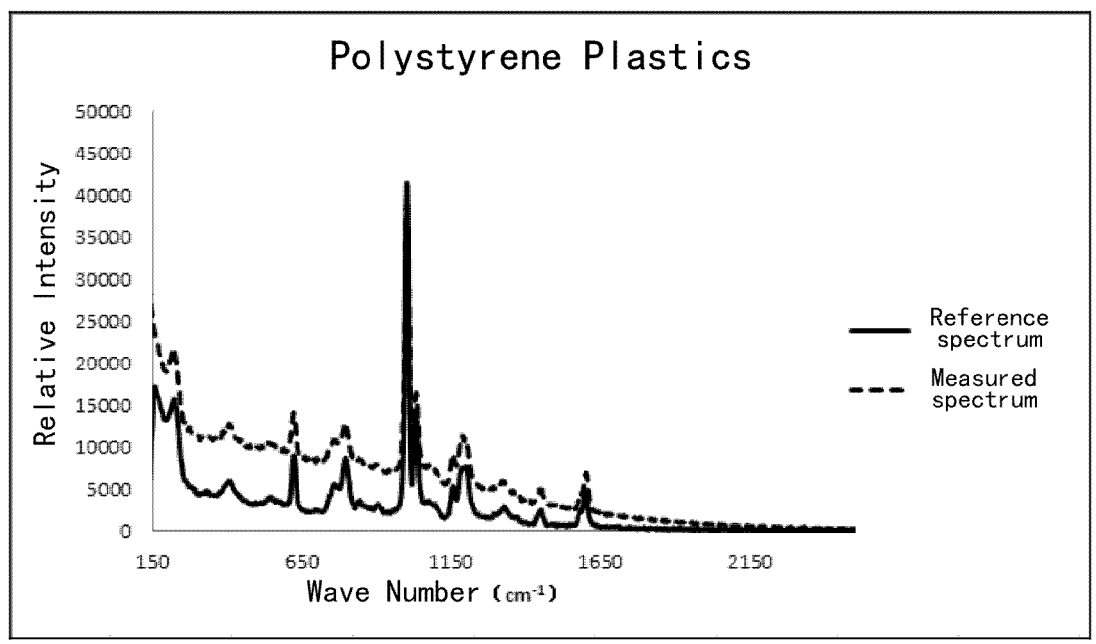

FIGS. 6-7 show identification examples of the gem identification method according to an embodiment of the present invention. FIG. 6 shows the identification result of a Hetian jade sample. In FIG. 6, the Raman spectrogram of the sample to be detected is represented by the dashed line while the reference Raman spectrogram of the Hetian jade is represented by the solid line. It can be seen clearly from FIG. 6 that the characterizing peaks in the Raman spectrogram of the sample to be detected is substantially identical to the reference Raman spectrogram. Thus, it can be determined that the sample to be detected is the Hetian jade.

In another example of identification, the identification result shown in FIG. 7 reveals that the Raman spectrogram of the sample to be detected is identical to the reference Raman spectrogram of polystyrene plastics. It means that the sample to be detected is a fake made of the polystyrene plastics.

Although the present invention has been explained with reference to the drawings, the embodiments shown in the drawings are only illustrative, instead of limiting the present invention.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What is claimed is:

1. A jewel and jade identification method, comprising steps of:
    (a) placing a sample to be detected over one or more light transmission holes on a carrying surface of an object table and emitting, by an optical probe disposed below the carrying surface, an exciting light onto the sample through the light transmission hole and then collecting a Raman scattered light from the sample by the optical probe, wherein diameters of the light transmission holes are variable;
    (b) acquiring a Raman spectrum curve of the sample from the collected Raman scattered light from the sample; and
    (c) comparing the Raman spectrum curve with a reference Raman spectrum library for jewels and jades to identify the sample,
    wherein focal position of the exciting light is located adjacent to the light transmission hole.

2. The jewel and jade identification method according to claim 1, further comprising, before the step (a), following step of:
    (o) measuring Raman spectra of reference samples of jewels and jades having known compositions and/or Raman spectra of fakes, to obtain reference Raman spectra so as to establish the reference Raman spectrum library.

3. The jewel and jade identification method according to claim 1 or 2, further comprising:
    (d) placing another sample to be detected over another light transmission hole on the carrying surface of the object table and moving the object table with respect to the optical probe in a horizontal direction such that the optical probe emits the exciting light onto the another sample through the another light transmission hole and collects a Raman scattered light from the another sample;
    (e) acquiring a Raman spectrum curve of the another sample from the collected Raman scattered light from the another sample; and
    (f) comparing the Raman spectrum curve of the another sample with the reference Raman spectrum library for jewels and jades to identify the another sample.

4. The jewel and jade identification method according to claim 1 or 2, wherein the step (c) comprises:
    (c1) calculating a similarity degree between the Raman spectrum curve and reference Raman spectrum curves in the reference Raman spectrum library.

5. The jewel and jade identification method according to claim 4, wherein the similarity degree is defined as $$\text{Corr} = \left(1 - \sqrt{1 - \frac{A(x) \cdot B(x)}{\sqrt{A(x) \cdot A(x)} \sqrt{B(x) \cdot B(x)}}}\right) \times 100\%,$$

where $A(x)$ is a Raman spectrum curve function of the sample to be detected and $B(x)$ is a reference Raman spectrum curve function.

6. The jewel and jade identification method according to claim 4, wherein the similarity degree is defined as $$\text{Corr} = \frac{\left(\left(A(x) - \frac{\sum_{i=1}^{n} A_i}{n}\right) \cdot \left(B(x) - \frac{\sum_{i=1}^{n} B_i}{n}\right)\right)^2}{\left(\left(A(x) - \frac{\sum_{i=1}^{n} A_i}{n}\right) \cdot \left(A(x) - \frac{\sum_{i=1}^{n} A_i}{n}\right)\right)} \times 100\%,$$

$$\left(\left(B(x) - \frac{\sum_{i=1}^{n} B_i}{n}\right) \cdot \left(B(x) - \frac{\sum_{i=1}^{n} B_i}{n}\right)\right)$$

where $A(x)$ is a Raman spectrum curve function of the sample to be detected, $B(x)$ is a reference Raman spectrum curve function, $A_1, A_2, \ldots, A_n$ are n sample points of the $A(x)$, and $B_1, B_2, \ldots, B_n$ are n sample points of the $B(x)$.

7. The jewel and jade identification method according to claim 4, wherein the similarity degree is defined as $$\text{Corr} = \left(1 - \frac{\sum_{i=1}^{n} |A_i - B_i|}{n}\right) \times 100\%,$$

where $A(x)$ is a Raman spectrum curve function of the sample to be detected, $B(x)$ is a reference Raman spectrum curve function, $A_1, A_2, \ldots, A_n$ are n sample points of the A(x), and $B_1, B_2, \ldots, B_n$ are n sample points of the B(x).

8. The jewel and jade identification method according to claim 4, wherein the step (c) further comprises, before the step (c1), the following steps of:
(c01) searching one or more characterizing peaks from the Raman spectrum curve;
(c02) calculating peak positions and peak widths of a found characterizing peaks and comparing the peak positions and peak width with those of characterizing peaks in the reference Raman spectrum curve to pre-select the reference Raman spectrum curve used in the calculation of the step (c1).

9. A jewel and jade identification apparatus comprising:
an object table having a carrying surface configured to carry a sample to be detected thereon, the carrying surface being formed with one or more light transmission holes corresponding to one or more measure positions respectively;
an optical probe disposed below the carrying surface and configured to emit an exciting light onto the corresponding measure position through one of the light transmission holes from the underside of the carrying surface and then collect a Raman scattered light from the sample from the corresponding measure position; and
a data process device configured to generate a Raman spectrum curve from the Raman scattered light collected from the sample and then compare the Raman spectrum curve with a reference Raman spectrum library for jewels and jades to identify the sample,
wherein diameters of the light transmission holes are variable and wherein focal position of the exciting light is located adjacent to the light transmission hole.

10. The jewel and jade identification apparatus according to claim 9, further comprising a shielding baffle and a sliding track carrying the shielding baffle, the shielding baffle being located above the carrying surface and being slidable in a vertical direction along the sliding track.

11. The jewel and jade identification apparatus according to claim 9 or 10, wherein the carrying surface has a first light transmission hole corresponding to a first measure position and a second light transmission hole corresponding to a second measure position, and the object table is movable with respect to the optical probe in a horizontal direction to switch the measure position corresponding to the optical probe between the first measure position and the second measure position.

* * * * *